United States Patent [19]
Drummond et al.

[11] Patent Number: 5,863,400
[45] Date of Patent: *Jan. 26, 1999

[54] ELECTROCHEMICAL CELLS

[75] Inventors: Humphrey John Jardine Drummond; Thomas William Beck, both of New South Wales, Australia

[73] Assignee: USF Filtration & Separations Group Inc., Timonium, Md.

[*] Notice: This patent issued on a continued prosecution application filed under 37 CFR 1.53(d), and is subject to the twenty year patent term provisions of 35 U.S.C. 154(a)(2).

[21] Appl. No.: 727,504
[22] PCT Filed: Apr. 12, 1995
[86] PCT No.: PCT/AU95/00207
 § 371 Date: Feb. 24, 1997
 § 102(e) Date: Feb. 24, 1997
[87] PCT Pub. No.: WO95/28634
 PCT Pub. Date: Oct. 26, 1995

[30] Foreign Application Priority Data

Apr. 14, 1994 [AU] Australia ............................. PM5068

[51] Int. Cl.⁶ ........................................................ G01N 27/26
[52] U.S. Cl. ........................................... 204/415; 204/403
[58] Field of Search ........................................ 204/403, 415

[56] References Cited

U.S. PATENT DOCUMENTS

| | | | |
|---|---|---|---|
| 4,224,125 | 9/1980 | Nakamura et al. | 204/195 B |
| 4,233,029 | 11/1980 | Columbus | 23/230 R |
| 4,254,083 | 3/1981 | Columbus | 422/55 |
| 4,259,165 | 3/1981 | Miyake | 204/415 |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,307,188 | 12/1981 | White | 435/4 |
| 4,374,013 | 2/1983 | Enfors | 204/195 B |
| 4,404,066 | 9/1983 | Johnson | 204/1 T |
| 4,431,004 | 2/1984 | Bessman et al. | 128/635 |
| 4,517,287 | 5/1985 | Scheibe et al. | 435/4 |

(List continued on next page.)

FOREIGN PATENT DOCUMENTS

| | | |
|---|---|---|
| 0 251 915 A2 | 1/1988 | European Pat. Off. . |
| 0 278 647 A2 | 8/1988 | European Pat. Off. . |
| 0 351 516 A2 | 1/1990 | European Pat. Off. . |
| 0 171 375 B1 | 5/1990 | European Pat. Off. . |
| 0 400 918 A1 | 12/1990 | European Pat. Off. . |
| 0 418 404 A1 | 3/1991 | European Pat. Off. . |
| 0 451 981 A2 | 10/1991 | European Pat. Off. . |
| 0 560 336 A1 | 9/1993 | European Pat. Off. . |
| 2 020 424 | 11/1979 | United Kingdom . |
| 2 201 248 | 8/1988 | United Kingdom . |
| 2 154 735 | 9/1995 | United Kingdom . |
| WO 89/08713 | 9/1989 | WIPO . |
| WO 92/15701 | 9/1992 | WIPO . |
| WO 95/16198 | 6/1995 | WIPO . |

OTHER PUBLICATIONS

Derwent Abstract Accession No. 92 119462/15, Class S03, JP,A, 04–62463 (Tokyo Yogyo K.K.) Feb. 27 1992.

Patent Abstracts of Japan, P–269, p. 166, JP, A,59–3345 (Hitachi Seisakusho K.K.) Jan. 10, 1994.

Primary Examiner—Bruce F. Bell
Attorney, Agent, or Firm—Knobbe, Martens Olson & Bear, LLP

[57] ABSTRACT

An electrochemical cell comprises a porous membrane (8) of electrically insulating composition, the membrane having pores (not illustrated) communicating from one side of the membrane to another, a working electrode (5) disposed on one side and a counter or pseudo-reference electrode (7) disposed on the other side. A target area (11) of one electrode is liquid permeable and extends over the surface of membrane (8) without blocking underlying pores of the membrane. Optional insulating layers (9,10) cover the electrodes (5,7) and opening defines the target area (11). Preferably, the porous membrane is impregnated with reagents, for example GOD/Ferricyanide.

26 Claims, 2 Drawing Sheets

U.S. PATENT DOCUMENTS

| | | | |
|---|---|---|---|
| 4,517,291 | 5/1985 | Seago | 435/14 |
| 4,545,382 | 10/1985 | Higgins eta l. | 128/635 |
| 4,629,563 | 12/1986 | Wrasidlo | 210/500.34 |
| 4,654,197 | 3/1987 | Litja et al. | 422/56 |
| 4,664,119 | 5/1987 | Bessman et al. | 204/415 |
| 4,711,245 | 12/1987 | Higgins et al. | 128/635 |
| 4,774,039 | 9/1988 | Wrasidlo | 264/41 |
| 4,790,925 | 12/1988 | Miller et al. | 204/415 |
| 4,900,424 | 2/1990 | Birth et al. | 204/409 |
| 4,919,770 | 4/1990 | Preidel et al. | 204/153.1 |
| 5,059,908 | 10/1991 | Mina | 324/444 |
| 5,064,516 | 11/1991 | Rupich | 204/415 |
| 5,120,420 | 6/1992 | Nankai et al. | 204/403 |
| 5,122,244 | 6/1992 | Hoenes et al. | 204/153.1 |
| 5,126,034 | 6/1992 | Carter et al. | 204/403 |
| 5,128,015 | 7/1992 | Szuminsky et al. | 204/403 |
| 5,141,868 | 8/1992 | Shanks et al. | 435/288 |
| 5,151,166 | 9/1992 | Harral et al. | 204/425 |
| 5,192,415 | 3/1993 | Yoshioka et al. | 204/403 |
| 5,229,282 | 7/1993 | Yoshioka et al. | 435/177 |
| 5,272,087 | 12/1993 | El Murr et al. | 435/291 |
| 5,320,732 | 6/1994 | Nankai et al. | 204/403 |
| 5,382,346 | 1/1995 | Uenoyama et al. | 204/403 |
| 5,384,028 | 1/1995 | Ito | 204/403 |
| 5,385,846 | 1/1995 | Kuhn et al. | 436/70 |
| 5,413,690 | 5/1995 | Kost et al. | 204/403 |
| 5,437,999 | 8/1995 | Diebold et al. | 435/288 |
| 5,508,171 | 4/1996 | Walling et al. | 205/777.5 |
| 5,509,410 | 4/1996 | Hill et al. | 128/637 |
| 5,527,446 | 6/1996 | Kosek et al. | 205/415 |
| 5,620,579 | 4/1997 | Genshaw et al. | 204/402 |
| 5,628,890 | 5/1997 | Carter et al. | 204/403 |

ELECTROCHEMICAL CELLS

This application is a '371 of PCT/AU95/00207 filed Apr. 12, 1995.

FIELD OF THE INVENTION

This invention relates to an improved electrochemical cell and to a method of detecting and measuring an analyte using such a device.

BACKGROUND OF THE INVENTION

The invention will be described with reference to a glucose biosensor but it should be understood that this use is illustrative only and the invention may be applied to other types of sensors or systems based on electrochemical cells e.g. high temperature filters, display items, instruments for chemical analysis, for example of heavy metals in waste water or the like.

Electrochemical glucose analysers such as those used by diabetics to monitor their blood sugar levels and in clinics or hospitals are based on reaction pathway (a):

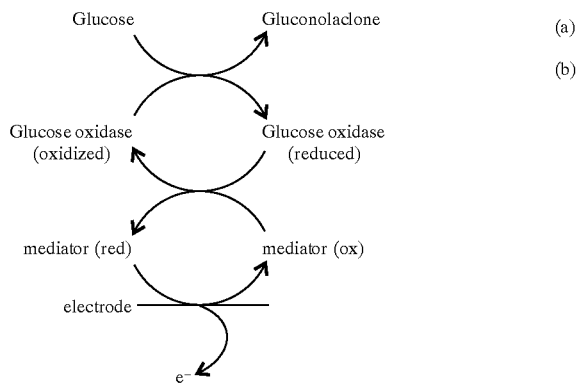

Typically, a sensor within an analyser comprises of a mediator which transfers electrons between an enzyme and an electrode as shown in reaction pathways (b) above. The signal produced upon such a transfer is processed and expressed as a function of the enzyme substrate, for example, the use of glucose oxidase (GOD) for the Measurement of glucose in blood or serum.

A known glucose sensor is a strip on one end of which is a predefined target or sample area and having three electrodes each attached lengthwise on the strip and across the target area. A silver chloride electrode in the middle forms a pseudo-reference electrode and the remaining two are known as working electrodes. Each working electrode is formed of a core of carbon paste. One of these electrodes is coated with a layer of GOD and mediator and the other with a layer of mediator such as ferrocene.

A drop of blood or sample amounting to about 25 $\mu$l is applied onto the target area and the strip is then inserted into a detector which measures the current at each of the working electrodes. This current corresponds to the oxidation of the ferrocene, and (at the working electrode containing GOD) the reoxidation of ferrocene produced by the reduction of mediator due to the reaction pathway described above. The difference in these currents is used to estimate the original glucose concentration in blood.

EP 289 269 describes a biosensor comprising a base sensor strip and an overlying exclusion layer or membrane which excludes red blood cells or regulates the flow of sample onto the sensor strip.

In WO 93/13408, a similar arrangement wherein a composite membrane welded to a housing containing electrodes is disclosed. The composite membrane consists of a porous membrane with an immobilized catalytic agent and at least one of a protecting or blocking membrane. The catalysed product flows from the composite membrane into an aperture defined within the housing to interact with the electrodes.

EP 230 472 discloses a perforated body such as nylon non-woven fabric positioned above an insulative base on which three electrodes are screen printed. A sample is applied above the perforated body and passes through it onto the base where an enzyme catalysed reaction occurs.

U.S. Pat. No. 4,431,507 discloses an electrode arrangement in which two working electrodes are dispersed on opposite sides of a porous membrane, one to prevent interfering materials contained in the test solution from being oxidized by the other working electrode.

The electrode arrangement is used in a cell having a buffer solution in which a counter and reference electrode are suspended.

DISCLOSURE OF THE INVENTION

The present invention is directed to a new and improved electrochemical cell which enables levels of analytes such as glucose to be measured precisely, conveniently and rapidly whilst using a small volume of sample. It provides a useful alternative to presently available sensors.

According to one aspect, the invention consists in an electrochemical cell comprising a porous membrane of electrically insulating composition, the membrane having pores communicating from one side of the membrane to another, a working electrode disposed on one side, a counter or pseudo-reference electrode disposed on the other side, and wherein a target area of at least one electrode is liquid permeable and extends over a surface of the porous membrane without blocking underlying pores of the membrane.

The working electrode is the electrode at which the electrochemical reaction that is being measured takes place. Where accurate definition of the potential of the working electrode is required, separate counter and reference electrodes may be used. The counter electrode completes the circuit and the reference electrode defines the potential of the working electrode. In many applications less accurate definition of the working electrode potential is required. In these cases the function of the reference electrode and counter electrode can be combined into a single electrode called a "pseudo-reference" or combined "counter/reference" electrode. In the present invention either a counter electrode or a pseudo-reference electrode is disposed on an opposite side of the membrane from the working electrode. In the present invention either a counter electrode or a pseudo-reference electrode is disposed on an opposite side of the membrane from the working electrode. If a reference electrode separate from the counter electrode is employed the reference electrode may be on the same side of the membrane as the counter electrode or on the working electrode side, or external to the membrane.

The porous membrane is preferably of a kind having pores which increase in diameter from a smooth or shiny side to a rough side. In particular, the porous membrane is desirably of the kind disclosed in U.S. Pat. Nos. 4,629,563 and 4,774,039 both of which are incorporated herein in their entirety by reference.

At least one of the electrodes must be formed so as not to block the underlying pores of the membrane so as to be permeable by a solution or suspension of an analyte. It is not essential that the electrode is porous over its entire area, but must be permeable to liquid in at least a target area.

Preferably, at least one electrode is formed by sputter deposition, electroless plating, electroplating, evaporation, anodization or the like on the surface of the membrane so as to form a continuous film on the surface of the membrane, the film not covering pore openings but defining the mouth of pore openings so that the electrode is permeable in a target area. In the case for example of a cell for determining glucose, the electrode porosity is sufficient to allow the passage therethrough of blood serum, the porosity being determined partly by the size of pore openings of the selected porous membrane. A preferred electrode film thickness is 10–200 nm, particularly 60–120 nm. Desirably both electrodes are sputtered or evaporated under partial vacuum and liquid permeable.

The target area is desirably defined by an opening in an insulating layer overlying one of the electrodes.

In a highly preferred embodiment, the electrochemical cell is used for determining glucose levels and thus comprises a GOD/ferricyanide treated membrane which fractionates serum from whole blood by virtue of its asymmetric porosity.

In another aspect of the invention, there is provided a process of producing an electrochemical cell, comprising the steps of disposing an electrode on each of two sides of a porous membrane, at least one of the electrodes being water permeable, storing a catalytic/mediator reagent in the porous membrane where desired, and defining a target area on one of the electrodes.

BRIEF DESCRIPTION OF DRAWINGS

An embodiment of the invention will now be described, by way of example only, with reference to the accompanying drawings in which.

DESCRIPTION OF PREFERRED EMBODIMENT OF THE INVENTION

Figure 1:
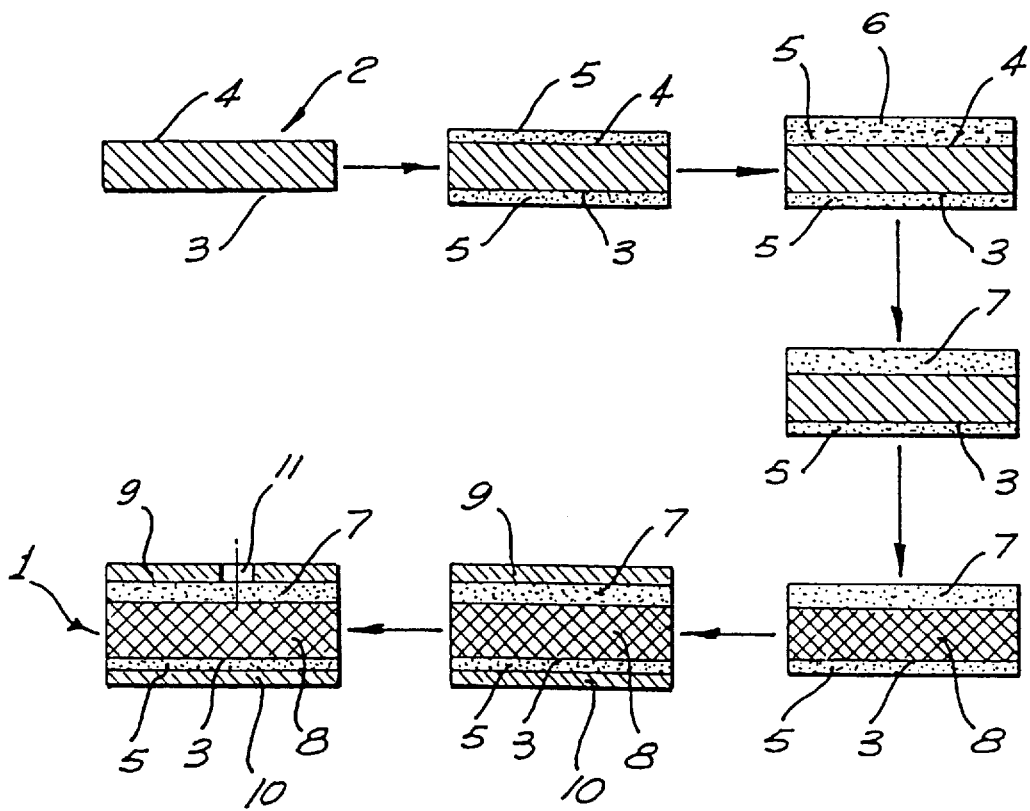
FIG. 1 is a schematic diagram showing a sequence of steps for manufacture of a glucose sensor 1 shown in side view cross-section.
Figures 2, 3:
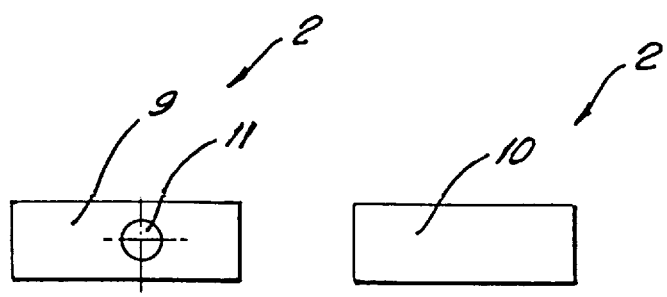
FIGS. 2 and 3 respectively show the top and bottom plan view of the biosensor 1.

A clean membrane 2 having small pores on the shiny or smooth side 3 and larger pores on the rough surface 4 is sputtered with gold to form working electrodes 5. The rough surface is additionally sputtered with silver at 6 and then chloridised to form a reference or counter electrode 7. The electrode coated membrane is then impregnated with a catalytic/mediator reagent 8 such as GOD/Fe $(CN)^{3-}_6$ after which layers 9, 10 of an electrically insulating composition are applied. A permeable target area 11 is defined on the membrane by punching an area from 9. The asymmetric, porous membrane 2 used is preferably made by a process disclosed in U.S. Pat. Nos. 4,629,563 and 4,774,039 and may comprise at least one polymer selected from polysulphones, polyamides, polyvinylidene halides, polyacrylonitriles, polycarbonates or the like. The thickness may be about 180 $\mu$, preferably from 30–150 $\mu$ with pore diameters of at least 10 kilodalton cut-off (lower limit) to 5 $\mu$m, and preferably from 0.2 $\mu$m to 0.5 $\mu$m. Membranes which are hydrophillic, inert and do not lyse red blood cells but aid separation of serum and red blood cells are especially preferred.

Although two gold working electrodes or working electrodes 5 are shown in FIG. 1, one working electrode on the smooth side is preferred, the electrode on the opposite side being a reference or counter or combined counter/reference electrode. In addition to gold, metals such as platinum, palladium, iridium, lead, a noble metal or an alloy may be used in forming the working electrodes. The working electrodes may be applied by sputtering, evaporation under partial vacuum, by electroless plating, by electroplating, or the like, so as to form a continuous film on the smooth face. When there are two working electrodes, they may be of different metals or alloys.

A counter or reference or combined counter/reference electrode may optionally be deposited on the rough face of the membrane by sputtering, evaporation under partial vacuum, electroless plating, electroplating, or the like. The counter or combined counter/reference electrode may, for example, be of gold, platinum, palladium, silver or other suitable metal. Nickel hydroxide or a silver halide may also be used to form the reference electrode. Silver chloride may be used although chloridisation may not be necessary if silver is used as sufficient chloride ions may be present in the blood sample.

The working and reference electrodes may be defined or patterned on the respective sides of the membranes using masks. Separate counter and pseudo-reference electrodes on the rough surface may also be defined using masks. This may remove the need for a silver halide or other reference electrode.

Masks may also be used to define the insulating layers. Such layers may be prepared by plasma polymerisation for example. Alternatively, impermeable layers may be laminated onto the membrane as insulation. However, the target area through which the sample interacts with the sensor or membrane should be free of such insulation. This may be achieved by punching or cutting out an area after the layers are applied. A small target area e.g. 1 mm square is preferred as one advantage of the new sensor is the requirement of a small volume of sample such as 1 $\mu$l, compared with about 25 $\mu$l in the prior art.

A laminate of support layer on the smooth, working electrode side may also be desirable as it will create a working electrode cavity, preventing cooling as a result of evaporation and also allow air to escape the working electrode cavity through grooves in the support layer, if present.

The impregnation of the membrane with preferred agents such as GOD/ferricyanide may be undertaken on an untreated membrane, on a membrane after electrodes have been applied or on a membrane after the insulating layers have been applied. The mediator may be impregnated in the oxidized or reduced state (e.g. ferricyanide or ferrocyanide). An oxidized mediator will minimize the initial current.

Any electrochemically interfering substances will be present at substantially constant concentration throughout the test. In contrast, the reduced mediator concentration will build up in concentration as the test progresses. Therefore a voltage pulse at the start of the test will measure predominantly the electrochemically interfering substance, whereas one at the end of the test will measure the electrochemically interfering substances plus the reduced mediator produced by turnover of the glucose. Subtraction of the first signal from the last will remove or reduce the effect of the electrochemically interfering substances. For example, an initial pulse of 0.1–10 seconds e.g. 2 seconds measures the effect of electrochemically interfering substances. A subsequent delay of 1 to 100 seconds e.g. 8 seconds is effected by disconnecting the electrodes after which a further pulse again measures the effect of electrochemically interfering substances. However, there is now an increased glucose dependent current due to the accumulation of reduced mediator near the electrode.

Other advantages of the instant invention are provided by the use of an asymmetrically porous membrane which fractionates serum and red blood cells, allowing a cleaner serum or substrate to interact with the reagents. Sample evaporation and/or interference is also reduced as the sample is able to held and "sheltered" within the membrane, again improving sensitivity of measurement. The dual acting membrane which serves as a fractionator and sensor allows a glucose measurement to be completed rapidly e.g. in up to about 20 seconds.

The sensitivity of the new sensor can be further improved by employing two working electrodes each poised at a different potential with either oxidized or reduced mediator or ferricyanide impregnated in the membrane thus allowing the electrodes to be switched in only during the last few seconds or continuously. The subtraction of one value from the other would further reduce effects of electrochemically interfering substances.

Similarly, the use of two working electrodes of different metals/alloys may further reduce the contribution by electrochemically interfering substances.

It will be understood that in use an apparatus is required to define the voltages applied to the electrodes and measure the resulting current.

Humidity and/or temperature sensors may optionally be incorporated in the apparatus to compensate for humidity or temperature effects.

Other variations may be employed without departing from the scope of the invention. Although the invention has been described with reference to a specific example, it will be appreciated by those skilled in the art that it may be embodied in many other forms. For instance, the electrochemical cell of the invention may be incorporated as a sensor into a pen- or needle-like analyser, a disposable strip or other devices for either external or in-vivo use.

Other uses of the invention include, for instance an array of thin electrodes or cells placed in a perpendicular fashion for electrochromic displays. As an example, overlapping electrodes could be used to address the elements in a slow-updating, large area display. The selective addressing of display elements in a large area may be achieved by a concentrated field through the porous electrode and membrane at the point where electrodes cross. An electrochromic material could be used to provide a colour change on the surface of the electrode. Different electrochromic materials could for instance be immobilized to the surface of each electrode to provide a colour display.

We claim:

1. An electrochemical sensor cell comprising a porous membrane of electrically insulating composition, the membrane having pores communicating from one side of the membrane to another,
   a working electrode disposed on one side,
   a counter or pseudo-reference electrode disposed on the other side,
   and wherein a target area of one electrode is liquid permeable and extends over a surface of the porous membrane without blocking underlying pores of the membrane.

2. An electrochemical sensor cell according to claim 1 wherein the membrane pore openings are of a larger cross-section on one membrane surface than on the opposite surface, and wherein said working electrode is on said opposite surface.

3. An electrochemical sensor cell according to claim 2 wherein the working electrode is on the side of the membrane having pore openings of smaller cross-section.

4. An electrochemical sensor cell according to claim 1 wherein working electrode comprises a metal selected from the group consisting of gold, platinum, palladium, iridium, lead and alloys thereof.

5. An electrochemical sensor cell according to claim 1 wherein the counter or pseudo-reference electrode is selected from gold, platinum, palladium, silver and silver chloride.

6. An electrochemical sensor cell according to claim 1 wherein the reference electrode comprises silver or silver chloride.

7. An electrochemical sensor cell according to claim 1 wherein the membrane is impregnated with one or more reagents.

8. An electrochemical sensor cell according to claim 7 wherein the membrane is impregnated with an enzyme and a mediator.

9. An electrochemical sensor cell according to claim 7 wherein the membrane is impregnated with GOD and a mediator.

10. An electrochemical sensor cell according to claim 1 wherein the membrane is impregnated with GOD/Ferricyanide.

11. An electrochemical cell according to claim 10 further incorporating a sample derived from blood such that, upon application of a voltage to said working electrode and said counter electrode, exhibiting a current flow occurs between said electrodes reflective of the concentration of glucose in said sample.

12. A method of detecting an analyte in a sample comprising the steps of contacting the sample with the target area of an electrochemical sensor cell according to claim 1.

13. A method of manufacture of an electrochemical sensor cell comprising the steps of disposing a working electrode on one side of a membrane, said membrane having pores communicating from one membrane side to the other, and disposing a counter or pseudo-reference electrode on the side of the membrane opposite the first, at least one of the electrodes being liquid permeable.

14. A method according to claim 13 wherein at least one of the electrodes is formed on a surface of the membrane.

15. A method according to claim 13 wherein the at least one an electrode is formed by deposition means selected from the group consisting of sputtering, electroless plating, electroplating, evaporation, and anodization.

16. A method according to claim 13 wherein said membrane pores are of larger cross-section on one side of the membrane than on the other, and wherein a working electrode is disposed on the side of the membrane having pores of lesser cross-section.

17. A method according to claim 16 wherein the membrane is hydrophillic, inert and does not lyse red blood cells.

18. A method according to claims 13 further comprising the step of covering the working electrode with an impermeable layer except at one or more target areas.

19. A method according to claim 13 further comprising the step of forming a reference electrode on the side of the membrane opposite the working electrode.

20. A method according to claim 19 wherein the reference electrode comprises silver and/or silver chloride.

21. A method according to claim 13 further comprising the step of forming a reference electrode on the same side as the working electrode.

22. A method according to claim 13 further comprising impregnating the porous membrane with one or more mediators.

23. A method according to claim 22 wherein the mediator is in an oxidized state.

24. A method according to claims 13 wherein the porous membrane is impregnated with GOD/Ferricyanide.

25. A method according to claim 13 further comprising the step of applying an electrically insulating composition over at least a part of an electrode surface.

26. A method according to claim 13 wherein the membrane comprises a polymer selected from the group consisting of polysulphones, polyamides, poly vinylidene halides, poly acrylonitriles and poly carbonates.

* * * * *